(12) United States Patent
Rüegg

(10) Patent No.: US 6,413,907 B2
(45) Date of Patent: Jul. 2, 2002

(54) HERBICIDAL COMPOSITION

(75) Inventor: Willy Rüegg, Gipf-Oberfrick (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/747,914

(22) Filed: Dec. 20, 2000

Related U.S. Application Data

(63) Continuation of application No. PCT/EP99/04373, filed on Jun. 24, 1999.

(51) Int. Cl.$^7$ .................. A01N 25/32; A01N 35/06; A01N 43/70; A01N 47/38
(52) U.S. Cl. ............. 504/105; 504/106; 504/107; 504/108; 504/133; 504/136; 504/137
(58) Field of Search ................. 504/103, 127, 504/133, 136, 137, 105, 106, 107, 108

(56) References Cited

U.S. PATENT DOCUMENTS

| | | | |
|---|---|---|---|
| 3,790,571 A | 2/1974 | Diskus et al. | 260/250 |
| 4,565,565 A | 1/1986 | Rohr et al. | 71/92 |
| 5,006,158 A | 4/1991 | Carter et al. | 71/90 |
| 5,183,492 A | 2/1993 | Suchy et al. | 504/243 |
| 5,498,773 A | 3/1996 | Noveroske et al. | 504/103 |
| 5,650,373 A | * 7/1997 | Ort et al. | 504/127 |

FOREIGN PATENT DOCUMENTS

| | | |
|---|---|---|
| EP | 0 298 680 | 1/1989 |
| EP | 0 338 992 | 10/1989 |
| EP | 0 551 650 | 7/1993 |
| EP | 0 613 618 | 9/1994 |
| EP | 0 614 606 | 9/1994 |
| WO | WO 97/34485 | 9/1997 |

OTHER PUBLICATIONS

Pesticide Manual,11th ed., British Crop Protection Council, (1997), Entry No. 412, 415, 414, 413, 493, 14, 6, 240, 34, 692, 651, 693, 595, 648, 146, 49, 339,495, 626, 88, 425, 664, 112,665, 436, 382, 589, 613, 644, 389, 519, 704, 497, 8, 383, 65, 557, 210, 100, 150, 192, 340, 359, 356, 341, 550, 37, 51, 383, 497, 8, 383, 65, 557, 210, 100, 150, 192, 340, 359, 356, 34, 550, 37, 51, 383, 61 (Formula 3.1, Benoxacor), 304, (Formula 3.2, Fenclorim), 154 (Formula 3.3, Cloquintocet), 462 (Formula, 3.4, Mefepyr–diethyl), 377 (Formula 3.5, Furilazol), 363 (Formula3.8, Fluxofenim), 213 (Formula 3.9, Dichlormid), 350 (Formula 3.10, Flurazole).

Agrow No. 296, Jan. 16, 1998, p. 21–22.

Agrow No. 261, Aug. 2, 196, p. 21.

The 1997 British Crop Protection Conference—Weeds, Conference Proceedings, vol. 1,2–8, pp. 67–72.

The 1997 British Crop Protection Conference—Weeds, Conference Proceedings, vol. 1, 3A–2, pp. 93–98.

Devine et al. Physiology of Herbicide Action. Section 17.4, "Safeners for herbicides". p. 376–387. 1993.*

* cited by examiner

*Primary Examiner*—S. Mark Clardy
(74) *Attorney, Agent, or Firm*—William A. Teoli, Jr.; Thomas Hamilton

(57) ABSTRACT

A herbicidal composition comprising, in addition to customary inert formulation assistants, a compound of formula I

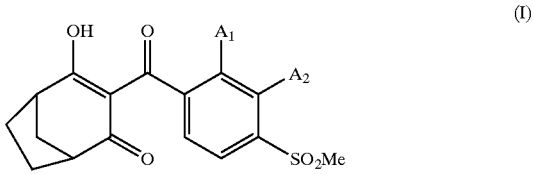

(I)

wherein either $A_1$ is nitro and $A_2$ is hydrogen or $A_1$ is methyl and $A_2$ is methoxy, and their salts, and b) a synergistically effective amount of one or more compounds selected from the compound of formula (2.1) to (2.33). The compositions according to the invention may also contain a safener.

12 Claims, No Drawings

HERBICIDAL COMPOSITION

This appln is a cont of Ser. No. PCT/EP99/04373 filed Jun. 24, 1996.

The present invention relates to a novel herbicidal synergistic composition that contains a combination of herbicides suitable for selectively controlling weeds in crops of cultivated plants, typically in crops of maize. The invention further relates to a process for controlling weeds in crops of cultivated plants and to the use of said novel composition for this purpose.

Compounds of Formula I

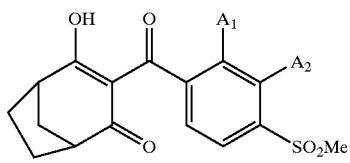
(I)

wherein either $A_1$ is nitro and $A_2$ is hydrogen or $A_1$ is methyl and $A_2$ is methoxy, and their salts, possess herbicidal activity, as is described for example in EP-A-0 338 992.

It has now surprisingly been shown that a combination of active compounds, in a ratio varying within specific limits, i.e. an active ingredient of formula I with one or more of the herbicides of formulae 2.1 to 2.33 listed below, which are known and are partly available commercially, exerts a synergistic effect that is able to control the majority of weeds occurring preferably in crops of cultivated plants preemergence as well as postemergence.

Accordingly, the present invention provides a novel synergistic composition for the selective control of weeds that, in addition to customary inert formulation assistants, contains as active ingredient a mixture of a) a compound of formula I

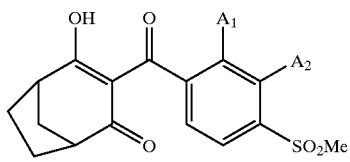
(I)

wherein either $A_1$ is nitro and $A_2$ is hydrogen or $A_1$ is methyl and $A_2$ is methoxy, as well as their salts, and b) a synergistically active amount of one or more compounds selected from the compound of formula 2.1

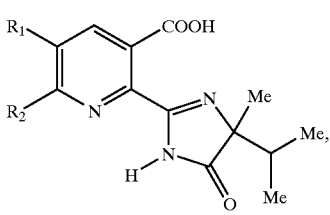
(2.1)

wherein
$R_1$ is $CH_2$—OMe, ethyl or hydrogen,
$R_2$ is hydrogen or $R_1$ and $R_2$ together are the group —CH=CH—CH=CH—;

and the compound of formula 2.2

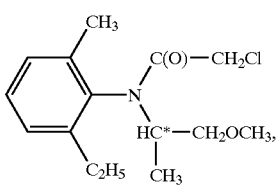
(2.2, <S>)

and the compound of formula 2.3

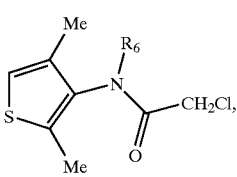
(2.3)

wherein $R_6$ is CH(Me)—$CH_2$OMe or <S>CH(Me)—$CH_2$OMe;

and the compound of formula 2.4

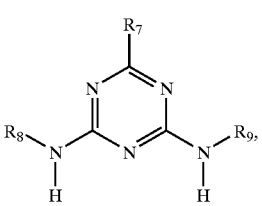
(2.4)

wherein $R_7$ is chlorine or SMe, $R_8$ is ethyl and $R_9$ is ethyl, isopropyl or tert.-butyl;

and the compound of formula 2.5

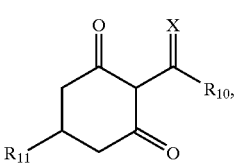
(2.5)

wherein $R_{10}$ is ethyl or n-propyl, $R_{11}$ is COO$^-$ 1/2 Ca$^{++}$, —$CH_2$—CH(Me)S—$CH_2CH_3$ or the group
and X is oxygen, N—O—$CH_2CH_3$ or N—O—$CH_2$CH=CH—Cl; and the compound of formula 2.6

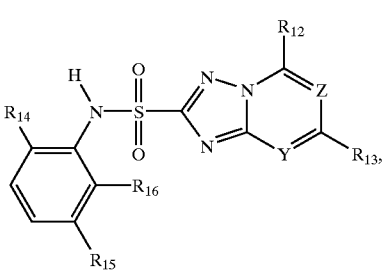
(2.6)

wherein $R_{12}$ is hydrogen, methoxy or ethoxy, $R_{13}$ is Me, methoxy or fluorine, $R_{14}$ is COOMe, fluorine or chlorine, $R_{15}$ is hydrogen or Me, Y is methane or nitrogen, Z is methane or nitrogen and $R_{16}$ is fluorine or chlorine;

and the compound of formula 2.7

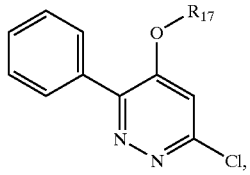
(2.7)

wherein $R_{17}$ is hydrogen or —C(O)—S-n-octyl;

and the compound of formula 2.8

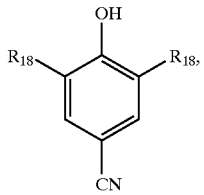
(2.8)

wherein $R_{18}$ is bromine or iodine;

and the compound of formula 2.9

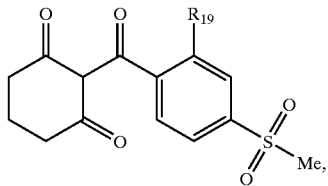
(2.9)

wherein $R_{19}$ is chlorine or nitro;

and the compound of formula 2.10

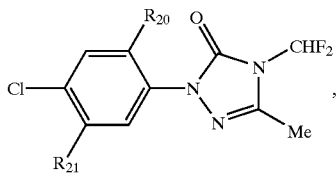
(2.10)

wherein $R_{20}$ is fluorine or chlorine and $R_{21}$ is —$CH_2$—CH(Cl)—$COOCH_2CH_3$ or —NH—$SO_2$Me;

and the compound of formula 2.11

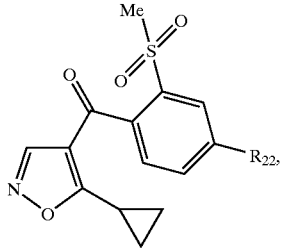
(2.11)

wherein $R_{22}$ is trifluoromethyl or chlorine;

and the compound of formula 2.12

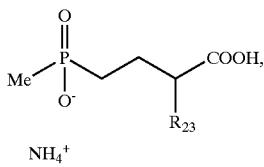
(2.12)

wherein $R_{23}$ is $NH_2$ or <S>$NH_2$;

and the compound of formula 2.13

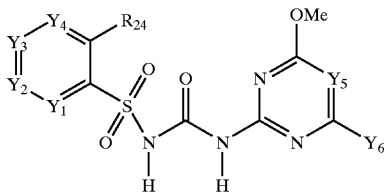
(2.13)

wherein $Y_1$ is nitrogen, methine or N—Me, $Y_2$ is nitrogen, methine or C—I, $Y_3$ is methine, $Y_4$ is methine, or $Y_3$ and $Y_4$ together are sulphur or C—Cl, $Y_5$ is nitrogen or methine, $Y_6$ is methyl or methoxy and $R_{24}$ is $CONMe_2$, COOMe, $CH_2$—$CH_2CF_3$ or $SO_2CH_2CH_3$, or the sodium salts thereof;

and the compound of formula 2.14

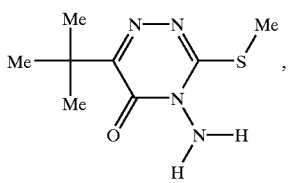
(2.14)

and the compound of formula 2.15

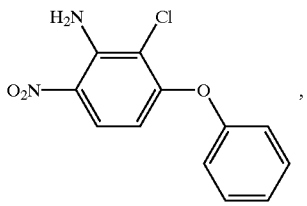
(2.15)

and the compound of formula 2.16

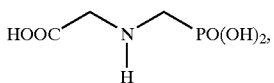
(2.16)

and the compound of formula 2.17

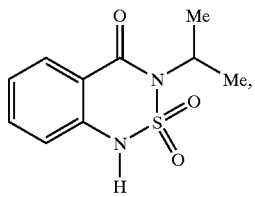
(2.17)

and the compound of formula 2.18

(2.18)

and the compound of formula 2.19

(2.19)

and the compound of formula 2.20

(2.20)

and the compound of formula 2.21

(2.21)

and the compound of formula 2.22

(2.22)

and the compound of formula 2.23

(2.23)

and the compound of formula 2.24

(2.24)

and the compound of formula 2.25

(2.25)

and the compound of formula 2.26

(2.26)

and the compound of formula 2.27

(2.27)

and the compound of formula 2.28

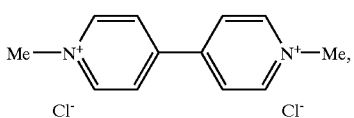
(2.28)

and the compound of formula 2.29

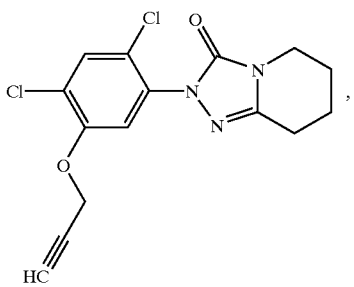
(2.29)

and the compound of formula 2.30

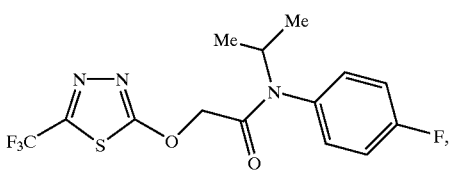
(2.30)

and the compound of formula 2.31

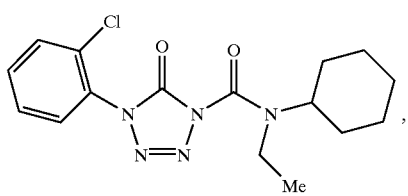
(2.31)

and the compound of formula 2.32

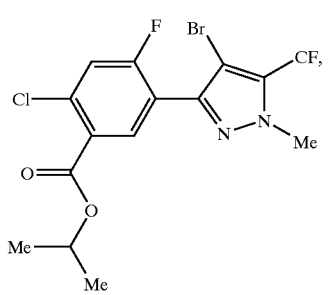
(2.32)

and the compound of formula 2.33

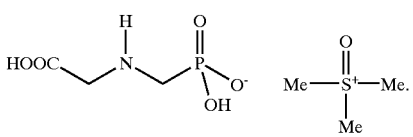
(2.33)

In the above formulae, "Me" signifies the methyl group. The invention also embraces the salts that the compounds of formula I are able to form with amines, alkali metal bases and alkaline earth metal bases or quarternary ammonium bases. Salt-forming alkali metal and alkaline earth metal hydroxides include the hydroxides of lithium, sodium, potassium, magnesium or calcium, those of sodium or potassium being especially preferred.

Illustrative examples of amines suitable for forming ammonium salts are ammonia, as well as primary, secondary, and tertiary $C_1$–$C_{18}$alkylamines, $C_1$–$C_4$hydroxyalkylamines and $C_2$–$C_4$alkoxyalkylamines, typically methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methyl ethylamine, methyl isopropylamine, methyl hexylamine, methyl nonylamine, methyl pentadecylamine, methyl octadecylamine, ethyl butylamine, ethyl heptylamine, ethyl octylamine, hexyl heptylamine, hexyl octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-nbutylamine, triisobutylamine, tri-sec-butylamine, tri-n-amylamine, methoxyethylamine and,ethoxyethylamine; heterocyclic amines such as pyridine, quinoline, isoquinoline, morpholine, piperidine, pyrrolidine, indoline, quinuclidine and azepine; primary arylamines such as anilines, methoxyanilines, ethoxyanilines, o-, m- and p-toluidines, phenylenediamines, benzidines, naphthylamines and o-, m- and p-chloroanilines. Preferred amines are triethylamine, isopropylamine and diisopropylamine. The compound of formula I, wherein $A_1$ is methyl and $A_2$ is methoxy, is most preferably present in the form of the diisopropylammonium salt.

It is entirely surprising that the combination of the compound of formula I with one or more herbicides selected from formulae 2.1 to 2.33 exceeds the expected additive action against the weeds to be controlled and thus in particular enhances the activity range of the individual components in two respects: On the one hand, the concentrations of the single compounds of formulae I and 2.1 to 2.33 are reduced whilst retaining good activity. On the other hand, the novel herbicidal combination also achieves a high degree of weed control where the single compounds have become no, longer agriculturally effective at low concentrations. The consequence is a substantial broadening of the activity spectrum against weeds and an additional increase in the selectivity for the cultivated plants that is necessary and desirable in the event of unintentional overapplication of herbicide. In addition, the novel composition permits greater flexibility with respect to subsequent crops while retaining the excellent control of weeds in crops of cultivated plants.

The composition of the invention may be used against a large number of agronomically important weeds, typically Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, *Sorghum halepense*, Rottboellia, Cyperus, Abutilon, Sida, Xanthium, Amaranthus, Chenopodium, Ipomoea, Chrysanthemum, Galium, Viola, and Veronica. The composition of this invention is suitable for all methods of application commonly used in agriculture, including preemergence application, postemergence application and seed dressing. The composition of the invention is preferably suitable for weed control in crops of cultivated plants, typically cereals, rape, sugar beet, sugar cane, plantations, rice, maize and soybeans and for the non-selective control of weeds.

Crops will also be understood as meaning those crops that have been made tolerant to herbicides or classes of herbicides by conventional breeding or genetic engineering methods.

The compounds of formulae 2.1 and 2.3 to 2.13 are known under the names imazamox, imazethapyr, imazaquin, imazapyr, dimethenamid, atrazine, terbutylazin, simazine, terbutyrn, prohexadione calcium, sethoxydim, clethodim, tepraloxydim, flumetsulam, metosulam, pyridate, bromoxynil, ioxynil, sulcotrione, carfentrazone, sulfentrazone, isoxaflutole, glufosinate, primisulfuron, prosulfuron, rimsulfuron, halosulfuron, nicosulfuron, and thifensulfuron and are described in the Pesticide Manual, eleventh ed., British Crop Protection Council, 1997 under the entry numbers 412, 415, 414, 413, 240, 34, 692, 651, 693, 595, 648, 146, 49, 339, 495, 626, 88, 425, 664, 112, 665, 436, 382, 589, 613, 644, 389, 519 and 704 The compound of formula 2.13, wherein $Y_1$, $Y_3$ and $Y_4$ are methine, $Y_2$ is C—I, $R_{24}$ is COOMe, $Y_5$ is nitrogen and $Y_6$ is methyl, is known under the name iodosulfuron (especially the sodium salt) from AGROW No. 296, Jan. $16^{th}$ 1998, page 22. The S-enantiomer of the compound of forrmula 2.12 is registered under CAS reg. no. [35597-44-5]. The compound of formula 2.2, aRS,1'S(-)N-(1'-methyl-2'-methoxyethyl)-N-chloroacetyl-2-ethyl-6-methylaniline, as well as a compound of the general formula 2.3, (1S,aRS)-2-chloro-N-(2,4-dimethyl-3-thienyl)-N-(2-methoxy-1-methylethyl)-acetamide, are described for example in WO 97/34485. The compound of formula 2.9, wherein $R_{19}$ is $NO_2$, is known under the name mesotrione and is described for example in U.S. Pat. No. 5,006,158. The compound of formula 2.6, wherein $R_{12}$ is ethoxy, $R_{13}$ is fluorine, Y is methine, $R_{14}$ is methoxycarbonyl, $R_{15}$ is hydrogen and $R_{16}$ is chlorine, is known under the name cloransulam, for example from AGROW no. 261, Aug. $2^{nd}$ 1996, page 21.

In addition, the following compounds of the composition according to the invention are described in the Pesticide Manual, eleventh ed., British Crop Protection Council, 1997:

| Compound of formula (name) | Pesticide Manual eleventh ed., Entry No.: |
|---|---|
| 2.14 (Metribuzin) | 497 |
| 2.15 (Aclonifen) | 8 |
| 2.16 (Glyphosate) | 383 |
| 2.17 (Bentazone) | 65 |
| 2.18 (Pendimethalin) | 557 |
| 2.19 (Dicamba) | 210 |
| 2.20 (Butylate) | 100 |
| 2.22 (Clomazone) | 150 |
| 2.23 (2,4-D) | 192 |
| 2.24 (Flumiclorac) | 340 |
| 2.25 (Fluthiacet-methyl) | 359 |
| 2.26 (Flurtamone) | 356 |
| 2.27 (Flumioxazin) | 341 |
| 2.28 (Paraquat) | 550 |
| 2.29 (Azafenidin) | 37 |
| 2.30 (Fluthiamid) | 51 |
| 2.33 (Sulfosate) | 383 |

The compound of formula 2.7, wherein $R_{17}$ is hydrogen, and the preparation thereof, are described in U.S. Pat. No. 3,790,571, the compound of formula 2.6, wherein $R_{12}$ is ethoxy, Z is nitrogen, $R_{13}$ is fluorine, $R_{14}$ is chlorine and $R_{15}$ is hydrogen and $R_{16}$ is chlorine, is described in U.S. Pat. No. 5,498,773.

The compound of formula 2.21 and the preparation thereof are described in U.S. Pat. No. 5,183,492, the compound of formula 2.22 is described under the name isoxachlortole in AGROW no. 296, Jan. $16^{th}$ 1998, page 22. The compound of formula 2.31 is described under the name fentrazamide in The 1997 British Crop Protection Conference—Weeds, Conference Proceedings Vol. 1, 2–8, pages 67 to 72, the compound of formula 2.32 is described under the name JV 485 (Isoxapropazol) in The 1997 British Crop Protection Conference—Weeds, Conference Proceedings Vol. 1, 3A-2, pages 93 to 98.

Preferred synergistic mixtures according to the invention contain as active ingredients a compound of formula I and either the compound of formula 2.2

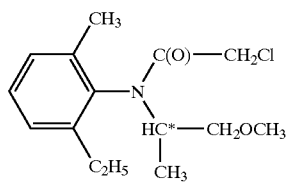

(2.2,aRS,1'S(-)N-(1'-methy-2'-methoxyethyl)-N-chloroacetyl-2-ethyl-6-methylaniline), or a compound of formula 2.3, or a compound of formula 2.4, wherein $R_7$ is chlorine, $R_8$ is ethyl and $R_9$ is isopropyl, or $R_7$ is chlorine, $R_8$ is ethyl and $R_9$ is tert.-butyl, or a compound of formula 2.6, wherein $R_{12}$ is hydrogen, Z is methine, $R_{13}$ is methyl, Y is nitrogen, $R_{14}$ is fluorine, $R_{15}$ is hydrogen and $R_{16}$ is fluorine, or $R_{12}$ is methoxy, Z is methine, $R_{13}$ is methoxy, Y is methine, $R_{14}$ is chlorine, $R_{15}$ is methyl and $R_{16}$ is chlorine, or a compound of formula 2.7, wherein $R_{17}$ is —C(O)—S-n-octyl, or a compound of formula 2.9, or a compound of formula 2.11, wherein $R_{22}$ is trifluoromethyl, or a compound of formula 2.12, or a compound of formula 2.13, wherein $Y_1$ is nitrogen, $Y_2$, $Y_3$ and $Y_4$ are methine, $R_{24}$ is dimethylaminocarbonyl and $Y_5$ is methine, or $Y_1$, $Y_2$, $Y_3$ and $Y_4$ are methine, $R_{24}$ is methoxycarbonyl and $Y_5$ is methine, or $Y_1$, $Y_2$, $Y_3$ and $Y_4$ are methine, $R_{24}$ is 3-trifluoropropyl and $Y_5$ is nitrogen, or $Y_1$ is nitrogen, $Y_2$, $Y_3$ and $Y_4$ are methine, $R_{24}$ is ethylsulphonyl and $Y_5$ is methine, or $Y_1$ is N—Me, $Y_2$ is nitrogen, $Y_3$ and $Y_4$ together are C—Cl, $R_{24}$ is methoxycarbonyl and $Y_5$ is methine, or a compound of formula 2.16, or a compound of formula 2.18, or a compound of formula 2.19, or a compound of formula 2.30.

A further group of preferred synergistic mixtures according to the invention contains as active ingredients a compound of formula I, the compound of formula 2.2

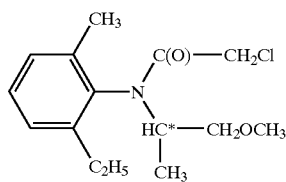

(2.2,aRS,1'S(-)N-(1'-methyl-2'-methoxyethyl)-N-chloroacetyl-2-ethyl-6-methylaniline), as well as a compound selected from formula 2.4, wherein $R_7$ is chlorine, $R_8$ is ethyl and $R_9$ is isopropyl, or $R_7$ is chlorine, $R_8$ is ethyl and $R_9$ is tert.-butyl, and of formula 2.6, wherein $R_{12}$ is hydrogen, Z is methine, $R_{13}$ is methyl, Y is nitrogen, $R_{14}$ is fluorine, $R_{15}$ is hydrogen and $R_{16}$ is fluorine, or $R_{12}$ is methoxy, Z is methine, $R_{13}$ is methoxy, Y is methine, $R_{14}$ is chlorine, $R_{15}$ is methyl and $R_{16}$ is chlorine, and of formula 2.7, wherein $R_{17}$ is —C(O)—S-n-octyl, and of formula 2.13, wherein $Y_1$ is nitrogen, $Y_2$, $Y_3$ and $Y_4$ are methine, $R_{24}$ is dimethylaminocarbonyl and $Y_5$ is methine, or $Y_1$, $Y_2$, $Y_3$ and $Y_4$ are methine, $R_{24}$ is methoxycarbonyl and $Y_5$ is methine, or $Y_1$, $Y_2$, $Y_3$ and $Y_4$ are methine, $R_{24}$ is 3-trifluoropropyl and $Y_5$ is nitrogen, or $Y_1$ is nitrogen, $Y_2$, $Y_3$ and $Y_4$ are methine, $R_{24}$ is ethylsulphony and $Y_5$ is methine, or $Y_1$ is N—Me, $Y_2$ is nitrogen, $Y_3$ and $Y_4$ together are C—Cl, $R_{24}$ is methoxycarbonyl and $Y_5$ is methine, and of formula 2.9, and of formula 2.11, wherein $R_{22}$ is trifluorometkyl, and of formula 2.12, and of formula 2.16, and of formula 2.18, and of formula 2.19.

It has been found that particularly effective herbicidal combinations are the combinations of compounds of formula I with the compound of formula 2.2

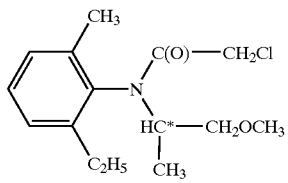

(2.2.,aRS,1'S(-)N-(1'-methyl-2'-methoxyethyl)-N-chloroacetyl-2-ethyl-6-methylaniline).

The composition according to the invention contains the active ingredient of formula I and the active ingredients of formulae 2.1 to 2.33 in any ratio, normally with an excess of one component over the others. In general, the mixture ratios (weight ratios) between the active ingredient of formula I and the components of formulae 2.1 to 2.33 lie between 1:2000 and 2000:1, especially between 200:1 and 1:200.

The rate of application can vary over a wide range and will depend on the nature of the soil, the type of application (pre- or postemergence), seed dressing, application to the seed furrow; no tillage application etc.), the cultivated plant, the weed to be controlled, the respective prevailing climatic conditions; and on other factors governed by,the type and time of application and the target crop. In general, the mixture according to the invention may be used at a rate of aplication of 1 to 5000 g of mixture/ha.

The mixtures of the compounds of formula I with the compounds of formulae 2.1 to 2.33 may be used in unmodified form, i.e. as obtained in the synthesis. Preferably, however, they are processed in conventional manner e.g. to emulsifiable concentrates, directly sprayable or dilutable solutions, dilute emulsions, wettable powders, soluble powders, dusts, granulates or microcapsules using the auxiliary agents customarily employed in formulation technology. As with the type of, compositions, the methods of application—such as spraying, atomising, dusting, wetting, scattering, or pouring—are selected in accordance with the intended objectives and the prevailing circumstances.

The formulations, i.e. the agents, preparations, or compositions containing the compounds of formula I and 2.1 to 2.33, and optionally one or more than one liquid or solid formulation assistant, are prepared in known manner, e.g. by homogeneously mixing and/or grinding the herbicide with said formulation auxiliaries, typically solvents or solid carriers. Surface-active compounds (surfactants) may additionally be used for preparing the formulations.

Examples of solvents and solid carriers are described in WO 97/34485, page 6.

Depending on the herbicide of formula I to be formulated, suitable surface-active compounds are nonionic, cationic and/or anionic surfactants and surfactant mixtures having good emulsifying, dispersing and wetting properties.

Examples of suitable anionic, non-ionic, and cationic surfactants are listed in WO 97/34485 on pages 7 and 8.

Also the surfactants customarily for the art of formulation and described, inter alia, in "Mc Cutcheon's Detergents and Emulsifiers Annual" MC Publishing Corp., Ridgewood N.J., 1981, Stache, H., "Tensid-Taschenbuch" (Handbook of Surfactants), Carl Hanser Verlag, Munich/Vienna, 1981, and M. and J. Ash, "Encyclopedia of Surfactants", Vol I–III, Chemical Publishing Co., New York, 1980–81 are suitable for manufacture of the herbicides according to the invention.

The herbicidal compositions will usually contain from 0.1 to 99% by weight, preferably from 0.1 to 95% by weight, of compound mixture of the compound of formula I and the compounds of formulae 2.1 to 2.33, from 1 to 99.9% by weight of a solid or liquid formulation assistant, and from 0 to 25% by weight, preferably from 0.1 to 25% by weight, of a surfactant.

Whereas it is customarily preferred to formulate commercial products as concentrates, the end user will normally use dilute formulations. The compositions may also contain further ingredients, such as: stabilisers, e.g., where appropriate epoxidised vegetable oils (epoxidised coconut oil, rapeseed oil, or soybean oil); antifoams, typically silicone oil; preservatives; viscosity regulators; binders; and tackifiers; as well as fertilisers or other chemical agents. Particularly preferred formulations are made up as follows: (%=percent by weight)

Emulsifiable Concentrates:

Compound mixture: 1 to 90%, preferably 5 to 20%

Surfactant: 1 to 30%, preferably 10 to 20%

Liquid carrier: 5 to 94%, preferably 70 to 85%

Dusts:

Compound mixture: 0.1 to 10%, preferably 0.1 to 5%

Solid carrier: 99.9 to 90%, preferably 99.9 to 99%

Suspension Concentrates:

Compound mixture: 5 to 75%, preferably 10 to 50%

Water: 94 to 24%, preferably 88 to 30%

Surfactant: 1 to 40%, preferably 2 to 30%

Wettable Powders:

Compound mixture: 0.5 to 90%, preferably 1 to 80%

Surfactant: 0.5 to 20%, preferably 1 to 15%

Solid carrier: 5 to 95%, preferably 15 to 90%

Granulates:

Compound mixture: 0.1 to 30%, preferably 0.1 to 15%

Solid carrier: 99.5 to 70%, preferably 97 to 85%

The invention is illustrated by the following non-limitative Examples.

| F1. Emulsifiable concentrates | a) | b) | c) | d) |
|---|---|---|---|---|
| Compound mixture | 5% | 10% | 25% | 50% |
| Calcium dodecylbenzenesulfonate | 6% | 8% | 6% | 8% |
| Polyethoxylated castor oil (36 mols EO) | 4% | — | 4% | 4% |
| Octylphenol polyethoxylate (7–8 mols EO) | — | 4% | — | 2% |
| Cyclohexanone | — | — | 10% | 20% |
| Aromatic hydrocarbon mixture $C_9$–$C_{12}$ | 85% | 78% | 55% | 16% |

Emulsions of any desired concentration can be prepared by diluting such concentrates with water.

| F2. Solutions | a) | b) | c) | d) |
|---|---|---|---|---|
| Compound mixture | 5% | 10% | 50% | 90% |
| 1-methoxy-3-(3-methoxy-propoxy)-propane | — | 20% | 20% | — |
| Polyethylene glycol mw 400 | 20% | 10% | — | — |
| N-Methyl-2-pyrrolidone | — | — | 30% | 10% |
| Aromatic hydrocarbon mixture $C_9$–$C_{12}$ | 75% | 60% | — | — |

The solutions are suitable for use in the form of microdrops.

| F3. Wettable powders | a) | b) | c) | d) |
|---|---|---|---|---|
| Compound mixture | 5% | 25% | 50% | 80% |
| Sodium ligninsulfonate | 4% | — | 3% | — |
| Sodium lauryl sulfate | 2% | 3% | — | 4% |
| Sodium diisobutylnaphthalene sulfonate | — | 6% | 5% | 6% |
| Octylphenol polyethoxylate (7–8 mols EO) | — | 1% | 2% | — |
| Highly dispersed silicic acid | 1% | 3% | 5% | 10% |
| Kaolin | 88% | 62% | 35% | — |

The compound is throughly mixed with the adjuvants and this mixture is ground in a suitable mill to give wettable powders that can be diluted with water to give suspensions of any desired concentration.

| F4. Coated granulates | a) | b) | c) |
|---|---|---|---|
| Compound mixture | 0.1% | 5% | 15% |
| Highly dispersed silicic acid | 0.9% | 2% | 2% |
| Inorganic carrier (Ø 0.1–1 mm) such as $CaCO_3$ or $SiO_2$ | 99.0% | 93% | 83% |

The compound mixture is dissolved in dichloromethane, the solution is sprayed on to the carrier, and the solvent is removed under vacuum.

| F5. Coated granulates | a) | b) | c) |
|---|---|---|---|
| Compound mixture | 0.1% | 5% | 15% |
| Polyethylene glycol mw 200 | 1.0% | 2% | 3% |
| Highly dispersed silicic acid | 0.9% | 1% | 2% |
| Inorganic carrier (Ø 0.1–1 mm) such as $CaCO_3$ or $SiO_2$ | 98.0% | 92% | 80% |

The finely ground active substance is uniformly applied in a mixer to the carrier moistened with polyethylene glycol. Non-dusty coated granulates are obtained in this manner.

| F6. Extruder granulates | a) | b) | c) | d) |
|---|---|---|---|---|
| Compound mixture | 0.1% | 3% | 5% | 15% |
| Sodium ligninsulfonate | 1.5% | 2% | 3% | 4% |
| Carboxymethylcellulose | 1.4% | 2% | 2% | 2% |
| Kaolin | 97.0% | 93% | 90% | 79% |

The compound is mixed and ground with the adjuvants, and the mixture is moistened with water. This mixture is extruded and then dried in a stream of air.

| F7. Dusts | a) | b) | c) |
|---|---|---|---|
| Compound mixture | 0.1% | 1% | 5% |
| Talcum or champagne chalk | 39.9% | 49% | 35% |
| Kaolin | 60.0% | 50% | 60% |

Ready-to-use dusts are obtained by mixing the active ingredient with the carriers and grinding on a suitable mill.

| F8. Suspension concentrates | a) | b) | c) | d) |
|---|---|---|---|---|
| Compound mixture | 3% | 10% | 25% | 50% |
| Ethylene glycol | 5% | 5% | 5% | 5% |
| Nonylphenol polyethoxylate (15 mols EO) | — | 1% | 2% | — |
| Sodium ligninsulfonate | 3% | 3% | 4% | 5% |
| Carboxymethylcellulose | 1% | 1% | 1% | 1% |
| 37% aqueous formaldehyde solution | 0.2% | 0.2% | 0.2% | 0.2% |
| Silicone oil emulsion | 0.8% | 0.8% | 0.8% | 0.8% |
| Water | 87% | 79% | 62% | 38% |

The finely ground active substance is intimately mixed with the adjuvants. In this way, a suspension concentrate is obtained from which suspensions of any desired concentration can be prepared by dilution with water.

It is often more convenient to formulate the active ingredient of formula I and the compound(s) 2.1 to 2.33 separately and not to combine them until shortly before application in the applicator in the desired mixing ratio in the form of a "ank mix" in water.

Biological Examples

A synergistic effect is always obtained when the herbicidal action of the combination of compound I and 2.1 to 2.33 is greater than the sum of the action of the individual herbicides.

The expected herbicidal action We for a given combination of two herbicides can be calculated as follows (q.v. COLBY, S. R., "Calculating synergistic and antagonistic response of herbicide combinations", Weeds 15, pages 20–22, 1967):

$$We = X + [Y \cdot (100-X)/100]$$

In This Formula:
  X = the percentage of herbicidal action after treatment with the compound of formula I at a rate of application of p kg per hectare, compared with untreated controls (=0%).
  Y = the percentage of herbicidal action after treatment with a compound of formula 2.1 to 2.33 at a rate of application of q kg per hectare, compared with untreated controls.
  We = the expected herbicidal action (percentage of herbicidal action compared with the untreated control plants) after treatment with the compounds of formulae I and 2.1 to 2.33 at a rate of application of p+q kg per hectare.

If the value actually observed is higher than the expected value We, then there is synergism.

The synergistic effect of the combinations of the compound of formula I with the compounds of formulae 2.1 to 2.33 is demonstrated in the following Examples.

Description of Postemergence Test

The test plants are grown under greenhouse conditions in plastic pots until reaching the 2–3 leaf stage. Standard soil is used, as the substrate for cultivation. At the 2–3 leaf stage, the herbicides are applied to the test plants on their own and in a mixture. Application is effected in the form of an aqueous suspension of the test substances in 500 l water/ha. The rates of application depend on the optimum dosages determined under field conditions and greenhouse conditions. Evaluation of the tests is made after 20 days (% activity, 100%=plant perished, 0%=no phytotoxic effect). The results are given in Tables 1 to 5 which follow.

The compound of formula I, wherein $A_1$ is nitro and $A_2$ is hydrogen, is designated as a compound of formula Ia. The compound of formula I, wherein $A_1$ is methyl and $A_2$ is methoxy, is designated as a compound of formula Ib.

TABLE 1

Synergistic effect of the mixture of the compound of formula Ia with halosulfuron:

| Test plant | Ia 75 g/ha | halosulfuron 100 g/ha | Ia 75 g/ha + halosulfuron 100 g/ha | expected activity We according to Colby |
|---|---|---|---|---|
| maize Dk 261 | 0 | 5 | 0 | 5 |
| Digitaria | 50 | 25 | 70 | 63 |

TABLE 2

Synergistic effect of the mixture of the compound of formula Ia with rimsulfuron:

| Test plant | Ia 150 g/ha | rimsulfuron 30 g/ha | Ia 150 g/ha + rimsulfuron 30 g/ha | expected activity We according to Colby |
|---|---|---|---|---|
| maize DK 261 | 5 | 10 | 5 | 14.5 |
| Rottboellia | 50 | 25 | 70 | 63 |

TABLE 3

Synergistic effect of the mixture of the compound of formula Ia with glyphosate:

| Test plant | Ia 150 g/ha | glyphosate 500 g/ha | Ia 150 g/ha + glyphosate 500 g/ha | expected activity We according to Colby |
|---|---|---|---|---|
| Cyperus | 60 | 75 | 95 | 90 |

TABLE 4

Synergistic effect of the mixture of the compound of formula Ia with primisulfuron:

| Test plant | Ia 75 g/ha | primisulfuron 20 g/ha | Ia 75 g/ha + primisulfuron 20 g/ha | expected activity We according to Colby |
|---|---|---|---|---|
| Echinochloa | 80 | 10 | 85 | 82 |

TABLE 5

Synergistic effect of the mixture of the compound of formula Ib with glyphosate

| Test plant | Ib 150 g/ha | glyphosate 500 g/ha | Ib 150 g/ha + glyphosate 500 g/ha | expected activity We according to Colby |
|---|---|---|---|---|
| Cyperus | 60 | 75 | 95 | 90 |

Description of Pre-emergence Test

The test plants are sown in plastic pots in standard soil under greenhouse conditions. Directly after sowing, the test substances are applied in an aqueous suspension (500 l water/ha). The test plants are then further cultivated in the greenhouse under optimum conditions. The rates of application depend on the optimum dosages determined under field conditions and greenhouse conditions. Evaluation of the tests is made after 26 days (% activity, 100% plant perished, 0%=no phytotoxic effect). The results are given in Tables 6 to 9 which follow.

TABLE 6

Synergistic effect of the mixture of the compound of formula Ia with terbutylazin:

| Test plant | Ia 100 g/ha | terbutylazin 200 g/ha | Ia 100 g/ha + terbutylazin 200 g/ha | expected activity We according to Colby |
|---|---|---|---|---|
| Ipomoea | 75 | 30 | 95 | 82.5 |
| Polygonum | 60 | 60 | 100 | 84 |
| Xanthium | 80 | 0 | 95 | 80 |

TABLE 7

Synergistic effect of the mixture of the compound of formula Ia with atrazine:

| Test plant | Ia 50 g/ha | atrazine 200 g/ha | Ia 50 g/ha + atrazine 200 g/ha | expected activity We according to Colby |
|---|---|---|---|---|
| Convolvulus | 75 | 80 | 100 | 95 |
| Polygonum | 40 | 90 | 100 | 94 |
| Xanthium | 60 | 0 | 98 | 60 |

TABLE 8

Synergistic effect of the mixture of the compound of formula Ib with terbutylazin:

| Test plant | Ib 50 g/ha | terbutylazin 200 g/ha | Ib 50 g/ha + terbutylazin 200 g/ha | expected activity We according to Colby |
|---|---|---|---|---|
| Convolvulus | 60 | 80 | 98 | 92 |
| Ipomoea | 60 | 30 | 75 | 72 |
| Polygonum | 30 | 60 | 100 | 72 |
| Xanthium | 70 | 0 | 98 | 70 |

TABLE 9

Synergistic effect of the mixture of the compound of formula Ib with atrazine:

| Test plant | Ib 50 g/ha | atrazine 200 g/ha | Ib 50 g/ha + atrazine 200 g/ha | expected activity We according to Colby |
|---|---|---|---|---|
| Convolvulus | 60 | 80 | 98 | 92 |
| Ipomoea | 60 | 70 | 100 | 88 |
| Polygonum | 30 | 90 | 100 | 93 |
| Xanthium | 70 | 0 | 100 | 70 |

It has surprisingly been found that special safeners are suitable for mixing with the synergistic composition according to the invention. The present invention therefore also relates to a selective herbicidal composition to control grasses and weeds in crops of cultivated plants, especially maize, which contains a compound of formula I, one or more compounds selected from the compounds of formulae 2.1 to 2.33 and a safener (antidote) and to protect the cultivated plants, :but not the weeds, from the phytotoxic action of the herbicide, and to the use of said composition for controlling weeds in crops of cultivated plants.

Accordingly, the invention also provides a selective herbicidal composition comprising, in addition to customary inert formulation assistants such as carriers, solvents and wetting agents, a mixture of a) herbicidally synergistic amount of a compound of formula I and one or more compounds selected from the compounds of formulae 2.1 to 2.33 and
b) to antagonise the herbicide, an antidotally effective amount of a safener selected from the compound of formula 3.1

(3.1)

and the compound of formula 3.2

(3.2)

and the compound of formula 3.3

(3.3)

O—CH$_2$—C(O)—O—CH(CH$_3$)C$_5$H$_{11}$-n, and the compound of formula 3.4

(3.4)

and the compound of formula 3.5

(3.5)

and the compound of formula 3.6

(3.6)

and the compound of formula 3.7

(3.7)

and the compound of formula 3.8

(3.8)

and of formula 3.9

Cl$_2$CHCON(CH$_2$CH=CH$_2$) (3.9), and of formula 3.10

(3.10)

and of formula 3.11

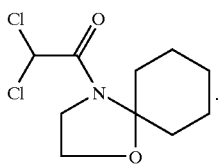
(3.11)

Preferred selective herbicidal compositions contain a) a herbicidally synergistic amount of a compound of formula I, a compound of formula 2.2

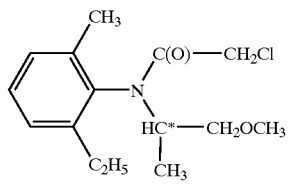

(2.2,aRS,1'S(−)N-(1'-methyl-2'-methoxyethyl)-N-chloroacetyl-2-ethyl-6-methylaniline), as well as a compound selected from formula 2.4, wherein $R_7$ is chlorine, $R_8$ is ethyl and $R_9$ is isopropyl, or $R_7$ is chlorine, $R_8$ is ethyl and $R_9$ is tert.-butyl, and of formula 2.6, wherein $R_{12}$ is hydrogen, Z is methine, $R_{13}$ is methyl, Y is nitrogen, $R_{14}$ is fluorine, $R_{15}$ is hydrogen and $R_{16}$ is fluorine, or $R_{12}$ is methoxy, Z is methine, $R_{13}$ is methoxy, Y is methine, $R_{14}$ is chlorine, $R_{15}$ is methyl and $R_{16}$ is chlorine, and of formula 2.7, wherein $R_{17}$ is —C(O)—S-n-octyl, and of ormula 2.13, wherein $Y_1$ is nitrogen, $Y_2$, $Y_3$ and $Y_4$ are methine, $R_{24}$ is dimethylaminocarbonyl and $Y_5$ is methine, or $Y_1$, $Y_2$, Y3 and $Y_4$ are methine, $R_{24}$ is methoxycarbonyl and $Y_5$ is methine, or $Y_1$, $Y_2$, $Y_3$ and $Y_4$ are methine, $R_{24}$ is 3-trifluoropropyl and $Y_5$ is nitrogen, or $Y_1$ is nitrogen, $Y_2$, $Y_3$ and $Y_4$ are methine, $R_{24}$ is ethylsulphonyl and $Y_5$ is methine, or $Y_1$ is N—Me, $Y_2$ is nitrogen, $Y_3$ and $Y_4$ together are C—Cl, $R_{24}$ is methoxycarbonyl and $Y_5$ is methine, and of formula 2.9, and of formula 2.11, wherein $R_{22}$ is trifluorormethyl, and of formula 2.12, and of formula 2.16, and of formula 2.18, and of formula 2.19, and b) to antagonise the herbicide, an antidotally effective amount of a safener of formula 3.1

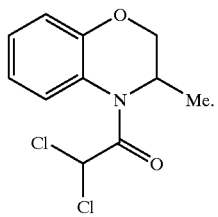
(3.1)

An especially preferred selective herbicidal composition contains a) a herbicidally synergistic amount of a compound of formula I and a compound of formula 2.2

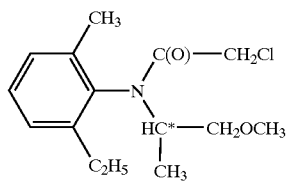

(2.2,aRS,1'S(−)N-(1'-methyl-2'-methoxyethyl)-N-chloroacetyl-2-ethyl-6-methylaniline) and b) to antagonise the herbicide, an antidotally effective amount of a safener of formula 3.1

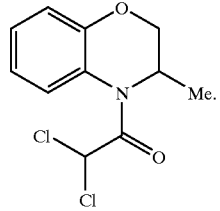
(3.1)

The invention also provides a selective herbicidal composition comprising, in addition to customary inert formulation assistants such as carriers, solvents and wetting agents, a mixture of a) a herbicidally effective amount of a compound of formula I and b) to antagonise the herbicide, an antidotally effective amount of a satener selected from the compound of formula 3.1

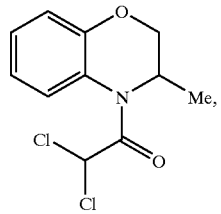
(3.1)

and the compound of formula 3.2

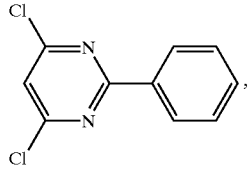
(3.2)

and the compound of formula 3.3

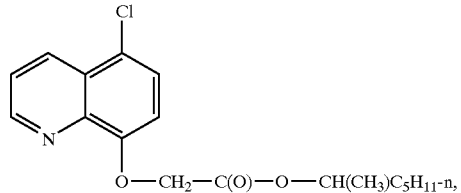
(3.3)

and the compound of formula 3.4

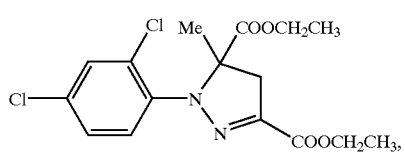
(3.4)

and the compound of formula 3.5

(3.5)

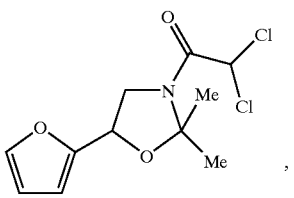

and the compound of formula 3.6

(3.6)

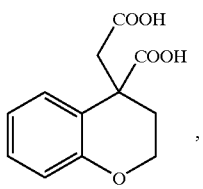

and the compound of formula 3.7

(3.7)

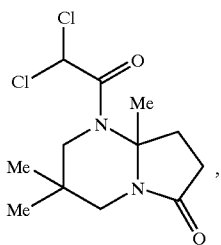

and the compound of formula 3.8

(3.8)

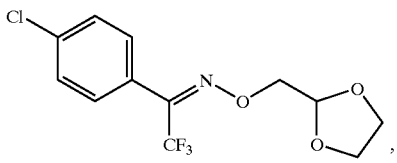

and of formula 3.9

$Cl_2CHCON(CH_2CH=CH_2)$ (3.9), and of formula 3.10

(3.10)

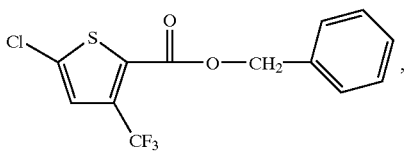

and of formula 3.11

(3.11)

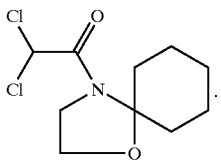

The invention additionally relates to a process for the selective control of weeds in crops of cultivated plants, which comprises treating said cultivated plants, the seeds or seedings or the crop area thereof with a herbicidally effective amount of the herbicide of formula I, if required, one or more herbicides selected from the compounds of formulae 201 to 2.33 and, to antagonise the herbicide, an antidotally effective amount of a safener of formula 3.1 to 3.11.

The compounds of formulae 3.1 to 3.11 are known and are described for example in the Pesticide Manual, eleventh ed., British Crop Protection Council, 1997 under the entry nos. 61 (formula 3.1, benoxacor), 304 (formula 3.2, fenclorim), 154 (formula 3.3, cloquintocet), 462 (formula 3.4, mefenpyr-diethyl), 377 (formula 3.5, furilazol), 363 (formula 3.8, fluxofenim), 213 (formula 3.9, dichlormid) and 350 (formula 3.10, flurazole) The compound of formula 3.11 is known under the designation MON 4660 (Monsanto).

The compound of formula 3.6 (AC 304415) is described for example in EP-A-0 613.618, and the compound of formula 3.7 is described in DE-A-2948535.

Crop plants which may be protected. against the harmful action of the above-mentioned herbicides by the safeners of formulae 3.1 to 3.11 are in particular cereals, cotton, soya, sugar beet, sugar cane, plantations, rape, maize and rice, especially maize. Crops will also be understood as meaning those crops that have been made tolerant to herbicides or classes of herbicides by conventional breeding or genetic engineering methods.

The weeds to be controlled may be monocot as well as dicot weeds, typically Stellaria, Agrostis, Digitaria, Avena, Apera, Brachiaria, Phalaris, Setaria, Sinapis, Lolium, Solanum, Echinochloa, Scirpus, Monochoria, Sagittaria, Panicum, Bromus, Alopecurus, Sorghum halepense, Sorghum bicolor, Rottboellia, Cyperus, Abutilon, Sida, Xanthium, Amaranthus, Chenopodium, Ipomoea, Chrysanthemum, Galium, Viola, and Veronica.

Crop areas will be understood as meaning the areas already under cultivation with the cultivated plants or seeds thereof, as well as the areas intended for cropping with said cultivated plants.

Depending on the end use, a safener of formula 3.1 to 3.11 can be used for pretreating seeds of the crop plants (dressing of seeds or seedlings) or it can be incorporated in the soil before or after sowing. It can, however, also be applied by itself alone or together with the herbicide postemergence. Treatment of the plant or the seeds with the safener can therefore in principle be carried out irrespective of the time of application of the herbicide. Treatment can, however, also be carried out by simultaneous application of the herbicide and safener (e.g. as tank mixture). The concentration of safener with respect to the herbicide will depend substantially on the mode of application. Where a field treatment is carried out either by using a tank mixture with a combination of safener and herbicide or by separate application of safener and herbicide, the ratio of herbicide to safener will usually be from 100:1 to 1:10, preferably 20:1 to 1:1. In field treatrtment it is usual to apply 0.001 to 1.0 kg/ha, preferably 0.001 to 0.25 kg/ha, of safener.

The concentration of herbicide is usually in the range from 0.001 to 2 kg/ha, but will preferably be from 0.005 to 0.5 kg/ha.

The compositions of this invention are suitable for all methods of application commonly used in agriculture, including preemergence application, postemergence application and seed dressing.

For seed dressing, 0.001 to 10 g of safener/kg of seeds, preferably 0.05 to 2 g of safener/kg of seeds, is usually applied. If the safener is used in liquid form shortly before sowing to effect soaking, then it is preferred to use safener solutions that contain the active ingredient in a concentration of 1 to 10000 ppm, preferably of 100 to 1000 ppm.

For application, it is preferred to process the safeners of formula 3.1 to 3.1 1, or mixtures of these safeners with the herbicide of formula I and optionally with one or rhore herbicides selected from formulae 2.1 to 2.33, conveniently together with the customary assistants of formulation technology to formulations, typically to emulsifiable concentrates, coatable pastes, directly sprayable or dilutable solutions, dilute emulsions, wettable powders, soluble powders, dusts, granulates or micrbcapsules.

Such formulations are described, for example, in WO 97/34485 on pages 9 to 13. The formulations are prepared in known manner, conveniently by homogeneously mixing and/or grinding the active ingredients with liquid or solid formulation assistants, typically solvents or solid carriers. Surface-active compounds (surfactants) may additionally be used for preparing the formulations. Solvents and solid carriers that are suitable for this purpose are described in WO 97/34485 on page 6.

Depending on the herbicide of formula I, 2.1 to 2.33 and 3.1 to 3.11 to be formulated, suitable surface-active compounds are nonionic, cationic and/or anionic surfactants and surfactant mixtures having good emulsifying, dispersing and wetting properties. Examples of suitable anionic, nonionic, and cationic surfactants are listed in WO 97/34485 on pages 7 and 8. Also the surfactants customarily used for the art of formulation and described, inter alia, in "Mc Cutcheon's Detergents and Emulsifiers Annual" MC Publishing Corp., Ridgewood N.J., 1981, Stache, H., "Tensid-Taschenbuch" (Handbook of Surfactants), Carl Hanser Verlag, Munich/Vienna, 1981, and M. and J. Ash, "Encyclopedia of Surfactants", Vol I–III, Chemical Publishing Co., New York, 1980–81 are suitable for manufacture of the herbicides according to the invention.

The herbicidal compositions will usually contain from 0.1 to 99% by weight, preferably from 0.1 to 95% by weight, of compound mixture of the compound of formula I, a compound selected from the compounds of formulae 2.1 to 2.33 and the compounds of formulae 3.1 to 3.11, from 1 to 99.9% by weight of a solid or liquid formulation assistant, and from 0 to 25% by weight, preferably from 0.1 to 25% by weight, of a surfactant. Whereas it is customarily preferred to formulate commercial products as concentrates, the end user will normally use dilute formulations.

The compositions may also contain further ingredients, such as stabilisers, e.g. where appropriate epoxidised vegetable oils (epoxidised coconut oil, rapeseed oil, or soybean oil), antifoams, typically silicone oil, preservatives, viscosity regulators, binders, tackifiers, as well as fertilisers or other chemical agents. Different methods and techniques-may suitably be used for applying the safeners of formula 3.1 to 3.11 or compositions containing them to protect cultivated plants from the harmful effects of herbicides of formula I and 2.1 to 2.33, for example the following:

i) Seed Dressing a) Dressing the seeds with a wettable powder formulation of the active ingredient of formulae 3.1 to 3.11 by shaking in a vessel until the safener is uniformly distributed on the surface of the seeds (dry treatment), In this instance, approximately 1 to 500 g of active ingredient of formula 3.1 to 3.11 (4 g to 2 kg of wettable powder) is used per 100 kg of seeds.

b) Dressing seeds with an emulsifiable concentrate of the active ingredient of formulae 3.1 to 3.1 1 by method a) (wet treatment).

c) Dressing by immersing the seeds in a mixture containing 100–1000 ppm of active ingredient of formulae 3.1 to 3.11 for 1 to 72 hours and where appropriate subsequently drying them (seed soaking).

In keeping with the natural environment, the preferred method of application is either seed dressing or treatment of the germinated seedlings, because the safener treatment is fully concentrated on the target crop. Usually 1 to 1000 g, preferably 5 to 250 g, of safener is used per 100 kg of seeds. However, depending on the method employed, which also permits the use of other chemical agents or micronutrients, the concentrations may deviate above or below the indicated limit values (repeat dressing).

ii) Application as a Tank Mixture

A liquid formulation of a mixture of safener and herbicide (reciprocal ratio from 10:1 to 1:100) is used, the concentration of herbicide being from 0.005 to 5.0 kg/ha. This tank mixture is applied before or after sowing.

iii) Application in the Furrow

The active ingredients of formulae 3.1 to 3.11 formulated as emulsifiable concentrate, wettable powder or granulate are applied to the open furrow in which the seeds have been sown. After covering the furrow, the herbicide is applied pre-emergence in conventional manner.

iv) Controlled Release of Compound

A solution of the active ingredients of formulae 3.1 to 3.11 is applied to a mineral granular carrier or to a polymerised granulate (urea/formaldehyde) and then dried. A coating can then be applied (coated granules) that allows the herbicide to be released at a controlled rate over a specific period of time.

Particularly preferred formulations are made up as follows:

(%=percent by weight)

Emulsifiable Concentrates:

Compound mixture: 1 to 90%, preferably 5 to 20%

Surfactant: 1 to 30%, preferably 10 to 20%

Liquid carrier: 5 to 94%, preferably 70 to 85%

Dusts:

Compound mixture: 0.1 to 10%, preferably 0.1 to 5%

Solid carrier: 99.9 to 90%, preferably 99.9 to 99%

Suspension Concentrates:

Compound mixture: 5 to 75%, preferably 10 to 50%

Water: 94 to 24%, preferably 88 to 30%

Surfactant: 1 to 40%, preferably 2 to 30%

Wettable Powders:

Compound mixture: 0.5 to 90%, preferably 1 to 80%

Surfactant: 0.5 to 20%, preferably 1 to 15%

Solid carrier: 5 to 95%, preferably 15 to 90%

Granulates:

Compound mixture: 0.1 to 30%, preferably 0.1 to 15%

Solid carrier: 99.5 to 70%, preferably 97 to 85%

The invention is illustrated by the following non-limitative Examples.

Formulation Examples for Mixtures of Herbicides of Formula I, Formulae 2.1 to 2.33 and Safeners of Formulae 3.1 to 3.11 (%=Percent by Weight)

| F1. Emulsifiable concentrates | a) | b) | c) | d) |
|---|---|---|---|---|
| Compound mixture | 5% | 10% | 25% | 50% |
| Calcium dodecylbenzenesulfonate | 6% | 8% | 6% | 8% |
| Polyethoxylated castor oil (36 mols EO) | 4% | — | 4% | 4% |
| Octylphenol polyethoxylate (7–8 mols EO) | — | 4% | — | 2% |
| Cyclohexanone | — | — | 10% | 20% |

| F1. Emulsifiable concentrates | a) | b) | c) | d) |
|---|---|---|---|---|
| Aromatic hydrocarbon mixture $C_9$–$C_{12}$ | 85% | 78% | 55% | 16% |

Emulsions of any desired concentration can be prepared by diluting such concentrates with water.

| F2. Solutions | a) | b) | c) | d) |
|---|---|---|---|---|
| Compound mixture | 5% | 10% | 50% | 90% |
| 1-methoxy-3-(3-methoxy-propoxy)-propane | — | 20% | 20% | — |
| Polyethylene glycol mw 400 | 20% | 10% | — | — |
| N-Methyl-2-pyrrolidone | — | — | 30% | 10% |
| Aromatic hydrocarbon mixture $C_9$–$C_{12}$ | 75% | 60% | — | — |

The solutions are suitable for use in the form of microdrops.

| F3. Wettable powders | a) | b) | c) | d) |
|---|---|---|---|---|
| Compound mixture | 5% | 25% | 50% | 80% |
| Sodium ligninsulfonate | 4% | — | 3% | — |
| Sodium lauryl sulfate | 2% | 3% | — | 4% |
| Sodium diisobutylnaphthalene sulfonate | — | 6% | 5% | 6% |
| Octylphenol polyethoxylate (7–8 mols EO) | — | 1% | 2% | — |
| Highly dispersed silicic acid | 1% | 3% | 5% | 10% |
| Kaolin | 88% | 62% | 35% | — |

The compound is throughly mixed with the adjuvants and this mixture is ground in a suitable mill to give wettable powders which can be diluted with water to give suspensions of any desired concentration.

| F4. Coated granulates | a) | b) | c) |
|---|---|---|---|
| Compound mixture | 0.1% | 5% | 15% |
| Highly dispersed silicic acid | 0.9% | 2% | 2% |
| Inorganic carrier (Ø 0.1–1 mm) such as $CaCO_3$ or $SiO_2$ | 99.0% | 93% | 83% |

The compound mixture is dissolved in dichloromethane, the solution is sprayed on to the carrier, and the solvent is removed under vacuum.

| F5. Coated granulates | a) | b) | c) |
|---|---|---|---|
| Compound mixture | 0.1% | 5% | 15% |
| Polyethylene glycol mw 200 | 1.0% | 2% | 3% |
| Highly dispersed silicic acid | 0.9% | 1% | 2% |
| Inorganic carrier (Ø 0.1–1 mm) such as $CaCO_3$ or $SiO_2$ | 98.0% | 92% | 80% |

The finely ground active substance is uniformly applied in a mixer to the carrier moistened with polyethylene glycol. Non-dusty coated granulates are obtained in this manner.

| F6. Extruder granulates | a) | b) | c) | d) |
|---|---|---|---|---|
| Compound mixture | 0.1% | 3% | 5% | 15% |
| Sodium ligninsulfonate | 1.5% | 2% | 3% | 4% |
| Carboxymethylcellulose | 1.4% | 2% | 2% | 2% |
| Kaolin | 97.0% | 93% | 90% | 79% |

The compound is mixed and ground with the adjuvants, and the mixture is moistened with water. This mixture is extruded and then dried in a stream of air.

| F7. Dusts | a) | b) | c) |
|---|---|---|---|
| Compound mixture | 0.1% | 1% | 5% |
| Talc | 39.9% | 49% | 35% |
| Kaolin | 60.0% | 50% | 60% |

Ready-to-use dusts are obtained by mixing the active ingredient with the carriers and grinding on a suitable mill.

| F8. Suspension concentrates | a) | b) | c) | d) |
|---|---|---|---|---|
| Compound mixture | 3% | 10% | 25% | 50% |
| Ethylene glycol | 5% | 5% | 5% | 5% |
| Nonylphenol polyethoxylate (15 mols EO) | — | 1% | 2% | — |
| Sodium ligninsulfonate | 3% | 3% | 4% | 5% |
| Carboxymethylcellulose | 1% | 1% | 1% | 1% |
| 37% aqueous formaldehyde solution | 0.2% | 0.2% | 0.2% | 0.2% |
| Silicone oil emulsion | 0.8% | 0.8% | 0.8% | 0.8% |
| Water | 87% | 79% | 62% | 38% |

The finely ground active substance is intimately mixed with the adjuvants. In this way, a suspension concentrate is obtained, from which suspensions of any desired concentration can be prepared by dilution with water.

It is often more convenient to formulate the active ingredients of formulae 1, 2.1 to 2.33 and 3.1 to 3.11 separately and not to combine them until shortly before application in the applicator in the desired mixing ratio in the form of a "tank mix" in water.

The ability of the safeners of formulae 3.1 to 3.11 to protect crops from the phytotoxic action of herbicides of formula I will be demonstrated in the examples which follow.

Biological Example: Safening Effect

The test plants are grown under greenhouse conditions in plastic pots until reaching the 4 leaf stage. At this stage, the herbicides are applied to the test plants both on their own and in mixtures with the test substances that are to be tested as safeners. Application is effected in the form of an aqueous suspension of the test substances, prepared from a 25% wettable powder [example F3, b)] at 500 l water/ha. 3 weeks after application, the phytotoxic effect of the herbicides on the cultivated plants, such as maize and cereals, is evaluated on a percentage scale. 100% indicates that the test plant has perished, 0% indicates no phytotoxic effect.

The results obtained in this test show! that the damage to the cultivated plant caused by the herbicide of formula I in combination with one or more herbicides selected from formulae 2.1 to 2.33 can be significantly reduced with the compounds of formulae 3.1 to 3.11.

The same results are obtained by formulating the mixtures in accordance with Examples F1, F2 and F4 to F8.

What is claimed is:

1. A herbicidal synergistic composition comprising, in addition to customary inert formulation assistants, as the active ingredient, a combination of
   a) a compound of formula I

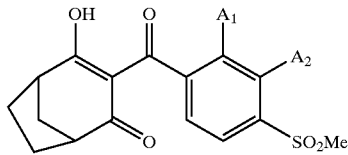

(I)

wherein either $A_1$ is nitro and $A_2$ is hydrogen or $A_1$ is methyl and $A_2$ is methoxy, as well as their salts, and
   b) a synergistically active amount of one or more compounds selected from the compound of formula 2.4

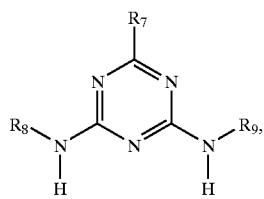

(2.4)

wherein $R_7$ is chlorine or SMe, $R_8$ is ethyl and $R_9$ is ethyl, isopropyl or tert.-butyl;
the compound of formula 2.13

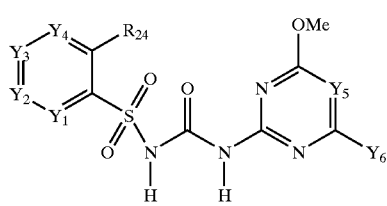

(2.13)

wherein $Y_1$ is nitrogen, methine or N—Me, $Y_2$ is nitrogen, methine or C—I, $Y_3$ is methine, $Y_4$ is methine, or $Y_3$ and $Y_4$ together are sulphur or C—Cl, $Y_5$ is nitrogen or methine, $Y_6$ is methyl or methoxy and $R_{24}$ is CONMe$_2$, COOMe, CH$_2$—CH$_2$CF$_3$ or SO$_2$CH$_2$CH$_3$, or the sodium salts thereof;
and the compound of formula 2.16

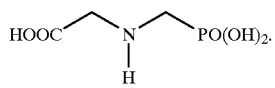

(2.16)

2. A herbicidal composition according to claim 1, comprising a compound of formula I and a synergistically effective amount either of a compound of formula 2.4, wherein $R_7$ is chlorine, $R_8$ is ethyl and $R_9$ is isopropyl, or $R_7$ is chlorine, $R_8$ is ethyl and $R_9$ is tert.-butyl, a compound of formula 2.13, wherein $Y_1$ is nitrogen, $Y_2$, $Y_3$ and $Y_4$ are methine, $R_{24}$ is dimethylaminocarbonyl and $Y_5$ is methine, or $Y_1$, $Y_2$, $Y_3$ and $Y_4$ are methine, $R_{24}$ is methoxycarbonyl and $Y_5$ is methine, or $Y_1$, $Y_2$, $Y_3$ and $Y_4$ are methine, $R_{24}$ is 3-trifluoropropyl and $Y_5$ is nitrogen, or $Y_1$ is nitrogen, $Y_2$, $Y_3$ and $Y_4$ are methine, $R_{24}$ is ethylsulphonyl and $Y_5$ is methine, or $Y_1$ is N—Me, $Y_2$ is nitrogen, $Y_3$ and $Y_4$ together are C—Cl, $R_{24}$ is methoxycarbonyl and $Y_5$ is methine, or a compound of formula 2.16.

3. A herbicidal composition according to claim 1, comprising a compound of formula I, a compound of formula 2.2

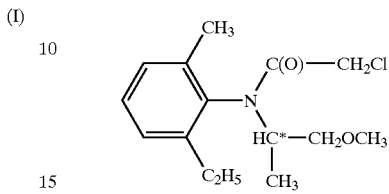

(2.2, aRS,1'S(-)N-(1'-methyl-2'-methoxyethyl)-N-chloroacetyl-2-ethyl-6-methylaniline), as well as a compound selected from formula 2.4, wherein $R_7$ is chlorine, $R_8$ is ethyl and $R_9$ is isopropyl, or $R_7$ is chlorine, $R_8$ is ethyl and $R_9$ is tert.-butyl, formula 2.13, wherein $Y_1$ is nitrogen, $Y_2$, $Y_3$ and $Y_4$ are methine, $R_{24}$ is dimethylaminocarbonyl and $Y_5$ is methine, or $Y_1$, $Y_2$, $Y_3$ and $Y_4$ are methine, $R_{24}$ is methoxycarbonyl and $Y_5$ is methine, or $Y_1$, $Y_2$, $Y_3$ and $Y_4$ are methine, $R_{24}$ is 3-trifluoropropyl and $Y_5$ is nitrogen, or $Y_1$ is nitrogen, $Y_2$, $Y_3$ and $Y_4$ are methine, $R_{24}$ is ethylsulphonyl and $Y_5$ is methine, or $Y_1$ is N—Me, $Y_2$ is nitrogen, $Y_3$ and $Y_4$ together are C—Cl, $R_{24}$ is methoxycarbonyl and $Y_5$ is methine, and of formula 2.16.

4. A herbicidal composition according to claim 1, wherein the compound of formula I is present in a weight ratio to the compounds of formulae 2.1 to 2.33 of 1:2000 to 2000:1.

5. A method of controlling undesirable plant growth in crops of cultivated plants, which comprises treating said plants or the locus thereof with a herbicidally effective amount of a composition as claimed in claim 1.

6. A method according to claim 5 wherein the cultivated plant is maize.

7. A method according to claim 5 which comprises treating the crops of cultivated plants with the said composition at rates of application corresponding to 1 to 5000 g total active ingredient per hectare.

8. Selective herbicidal composition comprising, in addition to customary inert formulation assistants, such as carriers, solvents and wetting agents, as active ingredient a mixture of
   a) herbicidally synergistic amount of a compound of formula I according to claim 1 and one or more compounds selected from the compounds of formulae 2.4, 2.13 and 2.16 according to claim 1 and
   b) to antagonise the herbicide, an antidotally effective amount of a safener selected from the compound of formula 3.1

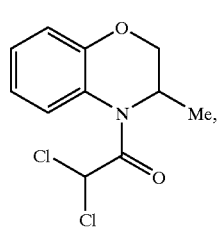

(3.1)

and the compound of formula 3.2

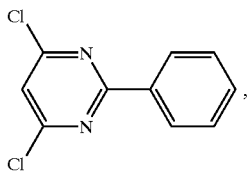
(3.2)

and the compound of formula 3.3

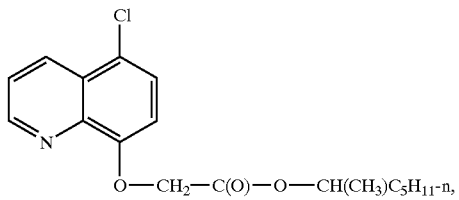
(3.3)

and the compound of formula 3.4

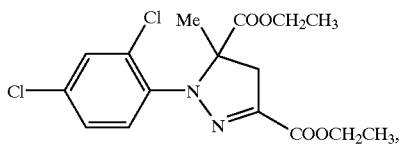
(3.4)

and the compound of formula 3.5

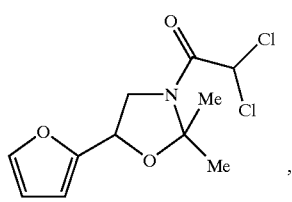
(3.5)

and the compound of formula 3.6

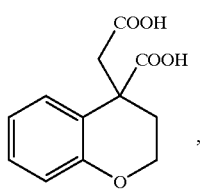
(3.6)

and the compound of formula 3.7

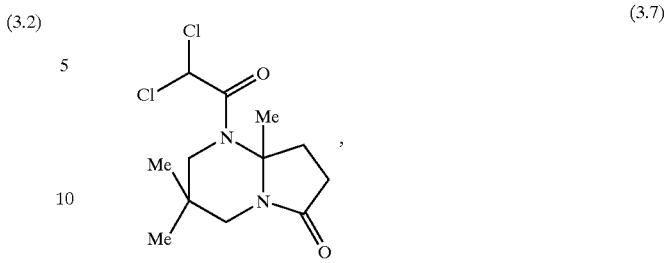
(3.7)

and the compound of formula 3.8

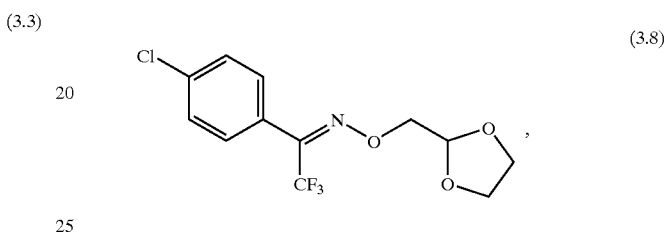
(3.8)

and of formula 3.9

$$Cl_2CHCON(CH_2CH=CH_2) \quad (3.9),$$

and of formula 3.10

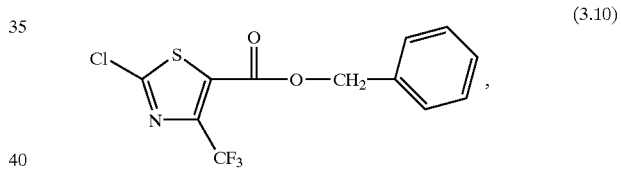
(3.10)

and of formula 3.11

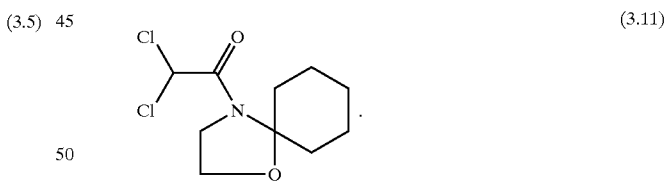
(3.11)

9. A method of selectively controlling weeds and grasses in crops of cultivated plants, which comprises treating said cultivated plants, the seeds or seedlings or the crop area thereof, with a herbicidally synergistic amount of a composition according to claim 8.

10. A method according to claim 9, wherein the rate of application of herbicides is 1 to 5000 g/ha and the rate of application.of safeners is 0.001 to 0.5 kg/ha.

11. A method according to claim 9 wherein the cultivated plant is maize.

12. Herbicidal composition according to claim 9, which contains a) a herbicidally synergistic amount of a compound of formula I, a compound of formula 2.2

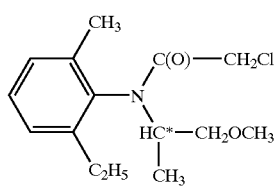

(2.2, aRS,1'S(−)N-(1'-methyl-2'-methoxyethyl)-N-chloroacetyl-2-ethyl-6-methylaniline), as well as a compound selected from formula 2.4, wherein $R_7$ is chlorine, $R_8$ is ethyl and $R_9$ is isopropyl, or $R_7$ is chlorine, $R_8$ is ethyl and $R_9$ is tert.-butyl, formula 2.13, wherein $Y_1$ is nitrogen, $Y_2$, $Y_3$ and $Y_4$ are methine, $R_{24}$ is dimethylaminocarbonyl and $Y_5$ is methine, or $Y_1$, $Y_2$, $Y_3$ and $Y_4$ are methine, $R_{24}$ is methoxycarbonyl and $Y_5$ is methine, or $Y_1$, $Y_2$, $Y_3$ and $Y_4$ are methine, $R_{24}$ is 3-trifluoropropyl and $Y_5$ is nitrogen, or $Y_1$ is nitrogen, $Y_2$, $Y_3$ and $Y_4$ are methine, $R_{24}$ is ethylsulphonyl and $Y_5$ is methine, or $Y_1$ is N—Me, $Y_2$ is nitrogen, $Y_3$ and $Y_4$ together are C—Cl, $R_{24}$ is methoxycarbonyl and $Y_5$ is methine, and of formula 2.16, and b) to antagonise the herbicide, an antidotally effective amount of a safener of formula 3.1

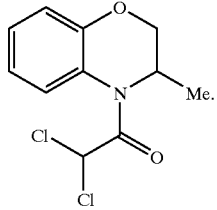

(3.1)

* * * * *